(12) United States Patent
Ham et al.

(10) Patent No.: US 10,004,776 B2
(45) Date of Patent: Jun. 26, 2018

(54) **PHARMACEUTICAL COMPOSITION FOR PREVENTING OR TREATING SKIN CANCER COMPRISING *PANAX* SPP. PLANT EXTRACT AND METHOD OF PREVENTING OR TREATING SKIN CANCER IN A SUBJECT USING THE SAME**

(71) Applicant: KOREA INSTITUTE OF SCIENCE AND TECHNOLOGY, Seoul (KR)

(72) Inventors: Jungyeob Ham, Gangneung-si (KR); Taejung Kim, Gangneung-si (KR); Kwantae Kim, Gangneung-si (KR); Pilju Choi, Gangneung-si (KR); Buyng Su Hwang, Gangneung-si (KR); Young Seok Kim, Gangneung-si (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 125 days.

(21) Appl. No.: 15/201,819

(22) Filed: Jul. 5, 2016

(65) Prior Publication Data
US 2017/0007653 A1    Jan. 12, 2017

(30) Foreign Application Priority Data

Jul. 10, 2015 (KR) ........................ 10-2015-0098474

(51) Int. Cl.
*A61K 36/00* (2006.01)
*A61K 36/258* (2006.01)
*A61K 9/00* (2006.01)

(52) U.S. Cl.
CPC .............. *A61K 36/258* (2013.01); *A61K 9/00* (2013.01); *A61K 2236/00* (2013.01)

(58) Field of Classification Search
None
See application file for complete search history.

(56) References Cited

FOREIGN PATENT DOCUMENTS

| KR | 2003-0080997 A | 10/2003 |
|---|---|---|
| KR | 10-2009-0089815 A | 8/2009 |
| KR | 10-1260047 B1 | 4/2013 |
| KR | 1260047 B1 * | 5/2013 |
| KR | 10-2013-0059659 A | 6/2013 |
| KR | 10-2013-0132264 A | 12/2013 |
| KR | 10-2014-0137955 A | 12/2014 |
| WO | 2013-176512 A1 | 11/2013 |
| WO | WO 2013/176512 A1 | 11/2013 |

OTHER PUBLICATIONS

Kim, Induction of apoptosis by ginsenoside Rk1 in SK-MEL-2-human melanoma. Archives of pharmacal research, (Mar. 2012) vol. 35, No. 4, pp. 717-722.*

Office Action of Korean Patent Application No. 10-2015-0098474 dated Nov. 10, 2016, which corresponds to the above-identified patent application.

Notice of allowance of Korean Patent Application No. 10-2015-0098474 dated May 16, 2017, which corresponds to the above-identified patent application.

* cited by examiner

*Primary Examiner* — Qiuwen Mi
(74) *Attorney, Agent, or Firm* — Goldilocks Zone IP Law

(57) ABSTRACT

Provided are a pharmaceutical composition for preventing or treating skin cancer and a method of preventing or treating skin cancer in a subject by using the pharmaceutical composition, wherein the pharmaceutical composition includes a *Panax* spp. plant extract as an active ingredient.

3 Claims, 3 Drawing Sheets

PHARMACEUTICAL COMPOSITION FOR PREVENTING OR TREATING SKIN CANCER COMPRISING *PANAX* SPP. PLANT EXTRACT AND METHOD OF PREVENTING OR TREATING SKIN CANCER IN A SUBJECT USING THE SAME

CROSS-REFERENCE TO RELATED APPLICATION

This application claims the benefit of Korean Patent Application No. 10-2015-0098474, filed on Jul. 10, 2015, in the Korean Intellectual Property Office, the disclosure of which is incorporated herein in its entirety by reference.

BACKGROUND

1. Field

One or more embodiments relate to a composition for preventing or treating skin cancer, and more particularly, to pharmaceutical composition for preventing or treating skin cancer, the composition comprising a *Panax* spp. plant extract containing 90% or more of Rg3, Rk1, and Rg5 with respect to a weight of ginsenoside Rb1, Rc, Rb2, Rd, Rg3, Rk1, and Rg5 obtainable by irradiating microwaves to a *Panax* spp. plant or an extract thereof as an active ingredient and method of method of preventing or treating skin cancer in a subject using the composition.

2. Description of the Related Art

Skin is a tissue that serves as a barrier at the outermost part of the body to protect various organs and muscles in the body from the external environment. The skin is the heaviest organ in the body, and its functions include heat-resistance and body temperature regulation. The skin serves as an organ that senses various stimuli such as temperature, pressure, and pain and involves in storage of lipid and water and synthesis of vitamin D. The term "skin cancer" refers to all types of malignant tumor that is formed in skin tissue. The skin cancer is mainly caused by environmental external stimuli, such as ultraviolet (UV) light, or genetic factors. Family history in certain genes, such as a KIT gene, has been known as having an influence on skin cancer. However, a factor known to have the most influence on skin cancer is external stimuli, such as UV light, occurrence of skin cancer has increased along with frequent outdoor activities as western lifestyle has been introduced, sun tanning and increased use of tanning devices, and increased amount of transmitted UV light due to a weakened ozone layer. When exposed to a large amount of UV light, thymidine dimmers may be formed or double-strand breakage may occur in DNAs in cells. When the damaged DNAs are not repaired properly, proto-oncogenes turn into oncogenes, and tumor suppressor genes may lose their functions. In this case, cell division regulation mechanisms in skin cells may not normally operate, which results in unlimited amplification, and thus normal cells are mutated into tumor cells. The cancerous tissue drags blood vessels nearby through hormone secretion to be supplied with nutrition, and, at the same time, the cancerous cells themselves are metastasized to other parts of the body through lymph nodes and blood vessels. A case when tumor occurred in skin is classified as 'primary' skin cancer, and a case when tumor started out from another organ and then metastasized and settled in skin is classified as 'metastatic' skin cancer, but skin cancer of general definition refers to primary skin cancer. Although skin cancer is one of the most common cancers in Caucasians, studies on skin cancer has not been actively conducted since it generally has a low fatality compared to those of cancers that occur in internal organs. However, skin cancer occupies 2.0% of all cancers occurred in the Republic of Korea based according to the statistics in 2012. Skin cancer can be diagnosed by using diagnostic devices such as computed tomography (CT) or ultrasound waves, as well as through observation with the naked eye and biopsy, but in many cases, the delay in initial discovery by taking the symptoms lightly may increase complete recovery rate and survival rate. The skin cancer may be classified into squamous cell carcinoma, basal cell carcinoma, or melanoma depending on which cells constituting skin tissue the skin cancer is derived from. Squamous cell carcinoma, which is a malignant tumor derived from epidermal keratinocytes, and basal cell carcinoma, which arises when the basal cell layer, the lowest layer of epidermis, or hair follicle cells turn into malignant tumor cells, are common skin cancers among those diagnosed in the Republic of Korea but have relatively low fatality. On the other hand, malignant melanoma is a cancer that originates from melanin cells, which determine color of skin, and has the highest degree of malignancy and easily penetrate and metastasize. Thus, malignant melanoma is a dangerous cancer as humans have a low survival rate with malignant melanoma.

*Panax ginseng* is a perennial plant belonging to the *Panax* species, Araliaceae family. Examples of *Panax* species plants having a similar efficacy to *Panax ginseng* include *Panax quinquefolia, Panax notoginseng, Panax japonica, Panax Trifolia, Panax pseudoginseng, Panax vietnamensis,* and the like. These *Panax* species plants contain dammarane-based saponin in common with 1 to 4 saccharide(s) combined to a dammarane backbone, unlike other plants. In particular, saponins contained at high concentration in *ginseng* include ginsenosides Rb1, Rb2, Rc, Rd, Rg1, and Re. These saponins have a variety of pharmaceutical effects that greatly differ in types and intensities depending on the structures thereof.

Formula 1

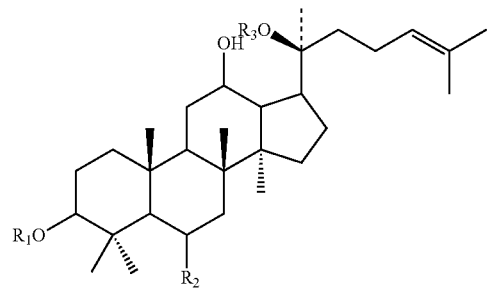

The dammarane-based saponin of the *Panax* species plants has protopanaxadiol (PPD) or protopanaxatriol (PPT) as a core nucleus, and may be classified as illustrated in Formula 1. A dammarane-based saponin may be classified according to $R_1$, $R_2$, and $R_3$ in Formula 1 as below

TABLE 1

| Group | Ginsenoside | R₁ | R₂ | R₃ |
|---|---|---|---|---|
| Protopanaxadiol (PPD) | Ra1 | -Glc-Glc | —H | -Glc-Ara(pyr)-Xyl |
| | Ra2 | -Glc-Glc | —H | -Glc-Ara(fur)-Xyl |
| | Ra3 | -Glc-Glc | —H | -Glc-Glc-Xyl |
| | Rb1 | -Glc-Glc | —H | -Glc-Glc |
| | Rb2 | -Glc-Glc | —H | -Glc-Ara(pyr) |
| | Rb3 | -Glc-Glc | —H | -Glc-Xyl |
| | Rc | -Glc-Glc | —H | -Glc-Ara(fur) |
| | Rd | -Glc-Glc | —H | -Glc |
| | Rg3(20-R,S) | -Glc-Glc | —H | —H |
| | Rh2(20-R,S) | -Glc | —H | —H |
| | Rs1 | -Glc-Glc-Ac | —H | -Glc-Ara(pyr) |
| | Rs2 | -Glc-Glc-Ac | —H | -Glc-Ara(fur) |
| | Rs3 | -Glc-Glc-Ac | —H | —H |
| | malonyl-Rb1 | -Glc-Glc-malonyl | —H | -Glc-Glc |
| | malonyl-Rc | -Glc-Glc-malonyl | —H | -Glc-Ara(fur) |
| | malonyl-Rd | -Glc-Glc-malonyl | —H | -Glc |
| | pseudoginsenoside F2 | -Glc | —H | -Glc |
| | notoginsenoside Fe | -Glc | —H | -Glc-Ara(fur) |
| Protopanaxatriol (PPT) | Re | —H | -OGlc-Rha | -Glc |
| | Ff | —H | -OGlc-Glc | —H |
| | Rg1 | —H | -OGlc | -Glc |
| | Rg2(20-R,S) | —H | -OGlc-Rha | —H |
| | Rh1(20-R,S) | —H | -OGlc | —H |
| | notoginsenoside R1 | —H | -OGlc-Xyl | -Glc |
| | notoginsenoside R2 | —H | -OGlc-Xyl | —H |
| | pseudoginsenoside F1 | —H | —OH | -Glc |
| | pseudoginsenoside F8 | -Glc-GlcAc | —OH | -Glc-Glc |
| | pseudoginsenoside F3 | —H | —OH | -Glc-Ara(pyr) |
| | Rh4 | —H | -OGlc | -methyl |

Rg5 and Rk1 are compounds that may be each respectively represented by Formulae 2 and 3, wherein $R_1$ is -Glc-Glc, and $R_2$ is —H.

Formula 2

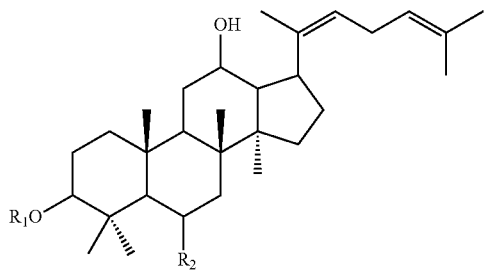

Formula 3

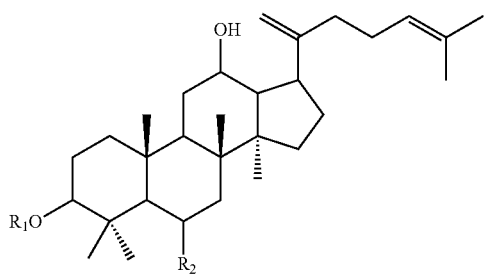

Protopanaxadiol-type ginsenosides Rb1 and Rb2 may produce 20(S)-Rg3 and 20(R)-Rg3 when -Glc-Glc or -Glc-Ara(pyr) is dissociated at position 20. Also, Rg5 and Rk1 may be produced when $H_2O$ is dissociated at position 20 of 20(S)-Rg3 and 20(R)-Rg3. Ginsenoside Rg5 is known for its antioxidative effects, promotion of brain function and cognitive function, blood vessel expansion effects, inhibitory effects on platelet aggregation, improving effects on dermatitis and/or psoriasis, and anti-inflammatory effects. Ginsenoside Rk1 is known for its blood vessels expansion effects, inhibitory effects on platelet aggregation, and improving effects on brain function and cognitive function such as memory and learning ability, prevention of dementia through the activation of brain cells, anti-aging and anti-cancer and cell regeneration. Ginsenoside Rk1 is known for its blood vessels expansion effects, inhibitory effects on platelet aggregation, and improving effects on brain function and cognitive function. Studies on a *ginseng* extract having a sufficiently increased content ratio of ginsenoside Rg5 and Rk1 is needed. Also, since ginsenoside Rg5 and Rk1 may be derived from ginsenoside Rg3, a ratio of ginsenoside (Rg5+Rk1)/(Rg3) is important in defining a content increase of Rg5 and Rk1.

The related conventional art has not disclosed whether a composition including a *Panax* spp. plant extract containing 90% or more of Rg3, Rk1, and Rg5 with respect to a weight of ginsenoside Rb1, Rc, Rb2, Rd, Rg3, Rk1, and Rg5 has prevention or treatment effects on skin cancer or not.

SUMMARY

As a result of trying to invent a preventing or treating agent that has less side effects and effectively removes melanoma cells, the present inventors have discovered that a pharmaceutical composition including a *Panax* spp. plant extract with an increased content ratio of ginsenoside Rg5+Rk1+Rg3 by microwave irradiation may induce apoptosis of skin cancer cells and thus has inhibiting effects on the survival of skin cancer cells. Thus, one or more embodiments include a pharmaceutical composition for preventing or treating skin cancer, the composition comprising a *Panax* spp. plant extract containing 90% or more of Rg3, Rk1, and Rg5 with respect to a weight of ginsenoside Rb1, Rc, Rb2, Rd, Rg3, Rk1, and Rg5 obtainable by irradiating microwaves to a *Panax* spp. plant or an extract thereof as an active ingredient; and a method of preventing or treating skin cancer by using the pharmaceutical composition.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
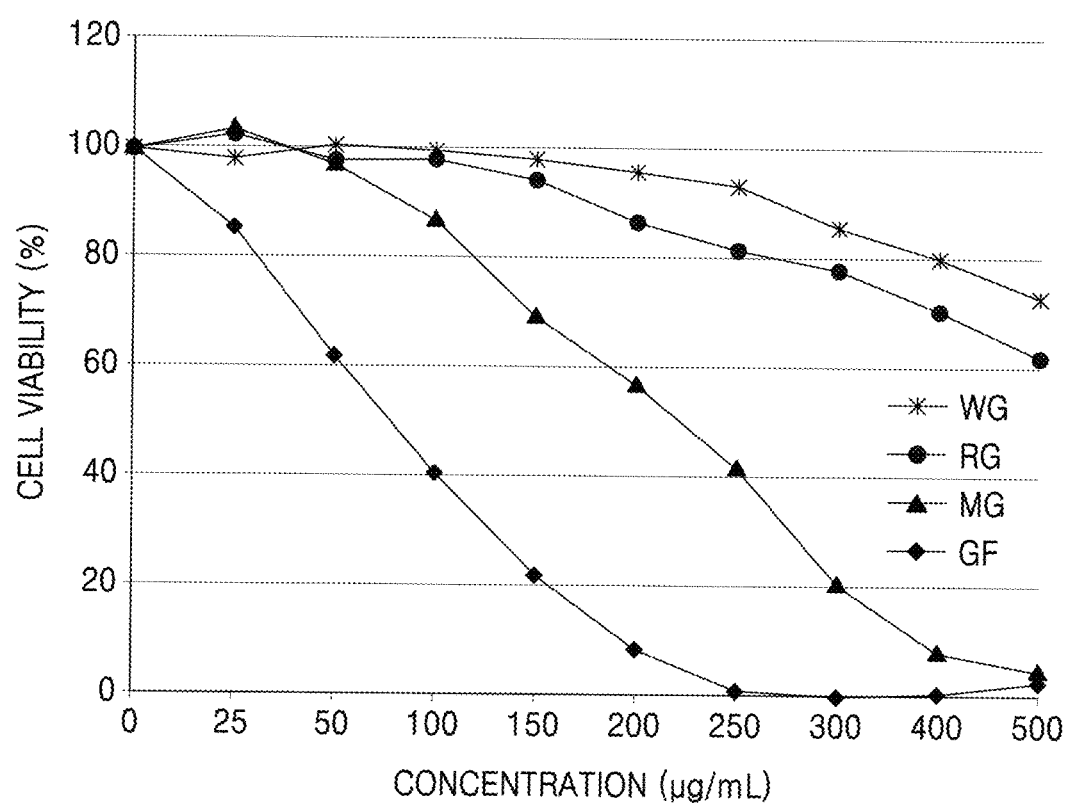
In FIG. 1, it was confirmed that a composition with an increased amount of ginsenoside according to an embodiment of the present invention has concentration-dependently suppressed a viability of human melanoma cells.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Unless otherwise defined, all technical terms used herein have the same meaning as commonly understood by one of ordinary skill in the art to which the present invention pertains. In addition, exemplary methods or samples are described in the present specification, but it should be understood that those similar or equivalent thereto are also encompassed in the scope of the invention. All references cited herein are hereby incorporated by reference.

According to an aspect of the present invention, provided is a pharmaceutical composition for preventing or treating skin cancer, wherein the pharmaceutical composition includes a *Panax* spp. plant extract containing 90% or more of Rg3, Rk1, and Rg5 with respect to a weight of ginsenoside Rb1, Rc, Rb2, Rd, Rg3, Rk1, and Rg5 obtainable by irradiating microwaves to a *Panax* spp. plant or an extract thereof as an active ingredient.

The present inventors have confirmed that a content ratio of ginsenoside Rg3+Rg5+Rk1 may increase by irradiating microwaves to a *Panax* spp. plant or an extract thereof. An extract obtainable by irradiating microwaves to the *Panax* spp. plant extract or a *Panax* spp. plant extract obtainable by extracting with an extraction solvent after irradiating microwaves to a *Panax* spp. plant may contain 90% or more of Rg3, Rk1, and Rg5 with respect to a weight of ginsenoside Rb1, Rc, Rb2, Rd, Rg3, Rk1, and Rg5 obtainable by irradiating microwaves to the *Panax* spp. plant or the extract thereof, compared to the case when a *Panax* spp. plant extract is simply heat-treated. For example, a content of Rg3, Rk1, and Rg5 with respect to a weight of ginsenoside protopanaxadiol, for example, Rb1, Rc, Rb2, Rd, Rg3, Rk1, and Rg5 may be from 90% to 100%, from 95% to 100%, from 98% to 100%, or 100%. Also, the microwave-irradiated process product may have a significantly high ratio of ginsenoside (Rg5+Rk1)/(Rg3), and, for example, (Rg5+Rk1)/(Rg3) may be at least 2, at least 3, at least 4, or at least 5. The microwave-irradiated process product has a higher content of ginsenoside Rg3+Rg5+Rk1, particularly Rg5 and Rk1, than the simple heat-treated process product and thus has an increased medicinal effect of ginsenoside Rg3+Rg5+Rk1, particularly of Rg5 and Rk1. Ginsenoside Rg3 is known for its nerve protecting functions, inhibitory effects on platelet aggregation, antioxidant effects, anti-inflammatory functions, kidney protecting functions, and antifatigue effects. Ginsenoside Rg5 is known for its antioxidative effects, improving effects on brain function and cognitive function, blood vessels expansion effects, inhibitory effects on platelet aggregation, improving effects on dermatitis and psoriasis, and anti-inflammatory effects. Ginsenoside Rk1 is mainly known for its blood vessels expansion effects, inhibitory effects on platelet aggregation, and improving effects on brain function and cognitive function. Thus, the microwave-processed *Panax* spp. plant or an extract thereof may have an increased amount of Rg3, Rg5, and Rk1, and thus the present inventors have proved anticancer inhibitory effects in view of cell viability by treating a skin cancer strain with the microwave-irradiated process product.

The microwave irradiation indicates thermal reaction heating a *Panax* spp. plant or a *Panax* spp. plant extract by irradiating microwaves thereto. The microwave may be a radio wave having a wavelength in a range of about 1 m to about 1 mm, and a frequency in a range of about 300 MHz to about 300 GHz. The heating by using microwaves may vary depending on an amount or state of a reactant. The microwave irradiation may be performed at a temperature in a range of 150° C. to 190° C., for example, 160° C. to 190° C., 170° C. to 190° C., 180° C. to 190° C., 150° C. to 180° C., 150° C. to 170° C., 150° C. to 160° C., 170° C. to 180° C., or 160° C. to 170° C. Also, the microwave irradiation may be performed for 30 minutes to 90 minutes, 30 minutes to 80 minutes, 30 minutes to 70 minutes, 30 minutes to 60 minutes, 30 minutes to 50 minutes, 30 minutes to 40 minutes, 40 minutes to 90 minutes, 50 minutes to 90 minutes, 60 minutes to 90 minutes, 70 minutes to 90 minutes, 80 minutes to 90 minutes, 50 minutes to 80 minutes, 60 minutes to 80 minutes, 70 minutes to 80 minutes, or 50 minutes to 70 minutes. The microwave irradiation may be performed under a pressure in a range of, for example, 1 atm to 100 atm, 2 atm to 100 atm, 5 atm to 100 atm, 7 atm to 100 atm, 10 atm to 100 atm, 15 atm to 100 atm, 1 atm to 80 atm, 2 atm to 80 atm, 5 atm to 80 atm, 7 atm to 80 atm, 10 atm to 80 atm, 15 atm to 80 atm, 1 atm to 50 atm, 2 atm to 50 atm, 5 atm to 50 atm, 7 atm to 50 atm, 10 atm to 50 atm, 15 atm to 50 atm, 1 atm to 30 atm, 2 atm to 30 atm, 5 atm to 30 atm, 7 atm to 30 atm, 10 atm to 30 atm, or 15 atm to 30 atm. The microwave irradiation may be performed in a neutral solution, for example, an aqueous solution. An output of the microwaves is not particularly limited and may be appropriately increased or decreased according to an amount of the reactant. For example, the output of the microwaves may be in a range of 50 W to 1000 W or 100 W to 700 W. Conditions for the microwave irradiation are not particularly limited thereto and may include arbitrary reaction conditions that allow a content of Rg3, Rk1, and Rg5 to be 90% or more with respect to a weight of ginsenoside protopanaxadiol, for example, Rb1, Rc, Rb2, Rd, Rg3, Rk1, and Rg5 by irradiating microwaves thereto. Also, the conditions for the microwave irradiation may include arbitrary reactions that allow a ratio of (Rg5+Rk1)/(Rg3) to be at least 2, at least 3, at least 4, or at least 5. The resultant of the microwave irradiation may be used as it is, or may be used in the form of a material that is dried or freeze-dried. According to an embodiment of the present invention, the microwave irradiation may be performed on an aqueous solution including a *Panax* spp. plant or a *Panax* spp. plant extract for 30 minutes to 90 minutes at a temperature of 150° C. to 190° C. under a pressure of, for example, 1 atm to 100 atm, 2 atm to 100 atm, 5 atm to 100 atm, 7 atm to 100 atm, 10 atm to 100 atm, 15 atm to 100 atm, 1 atm to 80 atm, 2 atm to 80 atm, 5 atm to 80 atm, 7 atm to 80 atm, 10 atm to 80 atm, 15 atm to 80 atm, 1 atm to 50 atm, 2 atm to 50 atm, 5 atm to 50 atm, 7 atm to 50 atm, 10 atm to 50 atm, 15 atm to 50 atm, 1 atm to 30 atm, 2 atm to 30 atm, 5 atm to 30 atm, 7 atm to 30 atm, 10 atm to 30 atm, or 15 atm to 30 atm. The *Panax* spp. plant may include at least one of ginsenoside protopanaxadiol, for example, Rb1, Rb2, Re, Rg1, Rc, and Rd. Examples of the *Panax* spp. plant may include, but are not limited to, *Panax ginseng*, *Panax quinquefolia*, *Panax notoginseng*, *Panax japonica*, *Panax trifolia*, *Panax pseudoginseng*, *Panax vietnamensis*, cultured roots thereof, heat-treated or enzyme-treated process products thereof, and combinations thereof. The heat-treated process products include red ginsengs or black ginsengs. For example, the *Panax* spp. plant may be *ginseng*.

The *Panax* spp. plant extract, which corresponds to the reactant of the microwave irradiation, may be an extract of an arbitrary *Panax* spp. plant including at least one of ginsenoside Rb1, Rb2, Rc, and Rd. The *Panax* spp. plant extract may further include Re and/or Rg1. The *Panax* spp. plant extract may be a crude extract or a product purified by additional solvent fraction or chromatography. For example, the extract of *Panax* spp. plant may be, for example, a crude extract of water, $C_1$-$C_4$ alcohol, or a mixture thereof of any *Panax* spp. plant; a solvent fraction of n-hexane, methylenechloride, ethylacetate, butanol or a mixture thereof of the crude extract; or a purified product of the solvent fraction. The crude extract of water, $C_1$-$C_4$ alcohol, or a mixture thereof may be, for example, a crude extract of methanol or ethanol, and when extracted, the amount of solvent used may be about 5 to about 15 times greater than that of the *Panax* spp. plant, for example, about 10 times. After adding the solvent to the *Panax* spp. plant, the *Panax* spp. plant may be extracted using one of general methods such as heating extraction, ultrasonic extraction, and reflux extraction, particularly, ultrasonic extraction. In the extraction process, the temperature of the solvent may be about 50° C. to about 200° C., about 50° C. to about 150° C., about 80° C. to about 200° C., or at about 120° C., but it is not limited thereto. In addition, the extraction time may be about 2 to about 4 hours, about 2 to about 3 hours, about 3 to about 4 hours, or about 3 hours, but it is not limited thereto. In addition, the extraction process may be performed once to five times, for example, three times, but it is not limited thereto. A crude extract obtained by the above-described method may be used as the extract of *Panax* spp. plant. Alternatively, a solvent fraction obtained by additionally extracting the crude extract with an organic solvent may be used as the extract of *Panax* spp. plant. The solvent fraction may be a fraction obtained by extracting the crude extract with methylenechloride, hexane, ethylacetate, butanol, or a mixture thereof, but it is not limited thereto. A further purified product of the solvent fraction described above may be used as the extract of *Panax* spp. plant. For example, at least one of ginsenoside Rb1, Rb2, Re, Rg1, Rc, and Rd may be further purified by column chromatography. The microwave-irradiated process product may contain 90% or more, 95% or more, or 98% or more of Rg3, Rk1, and Rg5 with respect to a total weight of ginsenoside in the obtained extract. The total weight of ginsenoside may be a total weight of protopanaxadiol, for example, Rb1, Rc, Rb2, Rd, Rg3, Rk1, and Rg5 or a total weight of Re, Rg1, Rb1, Rc, Rb2, Rd, Rg3, Rk1, and Rg5. The microwave irradiated process product is extracted by using a solvent and is not in a state of fraction.

In regard to the composition, the skin cancer may be squamous cell carcinoma, basal cell carcinoma, or melanoma. The skin cancer may be malignant melanoma. Malignant melanoma is a type of tumor that easily metastasizes, and once the tumor starts to metastasize, a 5-year survival rate of the patient is not high. In general, the foremost target during the treatment is to remove the most up to diffusion of unconfirmed cancer cells by excising all the way up to boundary tissues by performing a surgical operation, such as excision, as a basis of the treatment. Radiation therapy or anticancer chemotherapy is not significantly effective on melanoma, and melanoma is a cancer that is resistant to nearly all available anticancer drugs. In terms of other cancers, a significant number of drugs have been developed, where the drugs induce apoptosis on cancer cells that are not easily removed as they enter blood vessels or lymph nodes. However, drugs having these characteristics in terms of melanoma are still needed. Thus, if melanoma is not diagnosed at an initial stage and surgically removed, but metastasizes and dispersed to organs in the body, a survival rate of the patient may not be secured. In this regard, there is a great need of an anticancer agent capable of removing malignant melanoma as a target. The composition according to an embodiment of the present invention may be useful in prevention or treatment of skin cancer by using a mechanism of inducing apoptosis to reduce the survival of skin cancer cells.

The pharmaceutical composition according to the present invention may be formulated in the form of a general pharmaceutical formulation known in the art. The pharmaceutical formulation may include an orally-administered formulation, an injection, a suppository, a transdermallyadministered formulation, and transnasally-administered formulation. However, the pharmaceutical formulations are not limited to the above examples, and may be administered in the form of any formations. Preferably, the pharmaceutical composition may be formulated in the form of formulations for oral administration, including liquid dosage forms, such as solutions, emulsions, suspensions, extracts, or syrups, and solid dosage forms, such as powders, granules, tablets, capsules, or pills. When being formulated into each formulation, the pharmaceutical composition may be prepared by adding a pharmaceutically acceptable excipient or additive that is needed for the preparation of each formulation. For example, when formulating into a solid dosage form for oral administration, the pharmaceutically acceptable excipient may be at least one selected from a diluent, a lubricant, a binder, a disintegrant, a sweetener, a stabilizer, and a preservative. The excipient may be any excipients that are pharmaceutically acceptable. In particular, the excipient may be lactose, corn starch, soybean oil, microcrystalline cellulose, or mannitol, the lubricant may be magnesium stearate or talc, and the binder may be polyvinylpyrrolidone or hydroxypropylcellulose. In addition, the disintegrant may be calcium carboxymethyl cellulose, sodium starch glycolate, polacrilin potassium, or crospovidone. When formulating into a liquid dosage form for oral administration, various kinds of excipients, as well as a frequently used simple diluent, such as water or liquid paraffin, for example, a wetting agent, a sweetener, a flavoring agent, and a preservative, may be used. For example, the sweetener may be sucrose, fructose, sorbitol, or aspartame. The stabilizer may be sodium carboxymethyl cellulose, beta-cyclodextrin, bleached bees wax, or xanthan gum. The preservative may be methyl p-hydroxybenzoate, propyl p-hydroxybenzoate, or potassium sorbate. In addition, an additive of a solid or liquid oral formulation may be at least one selected from flavors, vitamins, and antioxidants. As a known flavoring agent in addition to the above-described ingredients, natural flavors such as Japanese apricot flavor, lemon flavor, pineapple flavor, and herb flavor; natural colors such as natural fruit juice, chlorophylin, or flavonoid; a sweetening ingredient such as fructose, honey, sugar alcohol, or sugar; or an acidifier such as citric acid or sodium citrate may be used in combination. The general pharmaceutical formulations may be appropriately prepared by those of ordinary skill in the art by using a general method that is well known in the art.

The pharmaceutical composition according to an embodiment of the present invention may be administered several times such that a total daily dosage of the microwave-irradiated process product as an active ingredient is about 0.01 mg/kg to 10 g/kg, preferably, about 1 mg/kg to about 1 g/kg per adult. The dosage may be appropriately increased or decreased according to an administration route, the degree of disease progress, gender, age, body weight, or clinical diagnosis of experts. The pharmaceutical composition may be used alone or along with operation, hormone therapy, chemotherapy, and a biological response modifier therapy for prevention or treatment of skin cancer and improving effects.

According to another aspect of the present invention, provided is a method of preventing or treating skin cancer in a subject, wherein the method includes administering a therapeutically effective amount of the said composition to a subject having skin cancer.

In the method, an administration route may be appropriately selected by those of ordinary skill in the art according to a state of the patient. The administration may be oral administration, parenteral administration, or topical administration. The administration may be topically performed on tissues having skin cancer. The administration may be topically performed on skin tissues.

In the method, as described above, a dosage may differ according to various factors such as a state of the patient, an administration route, and decision of experts. An effective dosage may be estimated from a capacity-reaction curve obtained by in vitro or animal-modeled experiments. A ratio and a concentration of a compound included in the composition according to an embodiment of the present invention that is subjected to be administered may be determined according to chemical characteristics, the administration route, and a therapeutic dosage. The dosage may be administered to a subject at an effective dose of about 1 μg/kg to about 1 g/kg per day, about 0.01 mg/kg to about 500 mg/kg per day, about 0.01 mg/kg to about 100 mg/kg per day, about 0.01 mg/kg to about 50 mg/kg per day, about 0.1 mg/kg to about 500 mg/kg per day, about 0.1 mg/kg to about 300 mg/kg per day, or about 0.1 mg/kg to about 100 mg/kg per day. The dose may change depending on an age, a body-weight, sensitivity, or symptoms of the subject. The subject may be a human.

Thereinafter, one or more embodiments of the present invention will be described in detail with reference to the following examples. However, these examples are not intended to limit the scope of the one or more embodiments of the present invention.

EXAMPLE 1

Preparation Of Microwave-processed *Ginseng* Extract

Dried *Panax ginseng* roots used in the present invention were purchased from herbal medicine shops in the Geumsan *ginseng* market, Korea. 6.0 L of 50% ethanol was added to 300 g of finely cut dried *ginseng* root powder, and the resultant mixture was reflux extracted at 80° C. for 3 hours to obtain a 50% ethanol extract. Thereafter, the obtained 50% ethanol extract was dried under reduced pressure to vaporize the solvent therefrom to obtain 76 g of a dried extract including ginsenoside Rb1, Rb2, Rc, Rd, Rg1, and Re. The 50% ethanol extract thus prepared was heat-treated. In particular, each of 25 g of the *ginseng* dry extracts was added to 50 mL of 50% ethanol in a 100 mL container of a microwave irradiator MARS5 manufactured by CEM (USA). The *ginseng* dry extract was irradiated with microwaves in the sealed container at a temperature of 150° C. and 1200 W power for 60 minutes. The microwave-irradiated *ginseng* dry extracts were freeze-dried to obtain microwave-irradiated process products. A maximum pressure for the microwave irradiation was 8.1 atm. A solvent was evaporated from the obtained *ginseng* extract microwave-irradiated process product to obtain 23 g of a dry process product including ginsenoside Rg3, Rk1, and Rg5. Amounts of Rg3, Rk1, and Rg5 with respect to a weight of Rb1, Rc, Rb2, Rd, Rg3, Rk1, and Rg5 in the prepared extract were 90% or more, as shown in Table 2.

EXAMPLE 2

Method of Isolating Ginsenoside from Microwave-processed *Ginseng*

3 g of the *ginseng* process product irradiated with microwaves according to Example 1 was sufficiently diluted in water having a 5-fold volume thereof, passed through a column filled with DIAION™ HP 20 resin (available from Samchun Chemicals), which is a nonpolar adsorption resin equilibrated with water, to adsorb a saponin component. DIAION™ HP 20 resin is a polystyrene resin having a surface of a particle that is hydrophobic, and thus a hydrophobic group of an organic molecule is adsorbed when an organic material is adsorbed. A polystyrene resin has a relatively large surface area (typically, about 450 m$^2$/g to about 900 m$^2$/g), a high porosity (a pore volume, typically, about 0.6 mL/g to about 1.8 mL/g), and a large average pore size (typically, about 100 Å to about 800 Å), which combines with a rough particle size (typically, about 20 mesh to about 60 mesh, wet) and thus provides a large capacity for a high extract flow rate and retention of a target compound. Therefore, an organic compound having a high hydrophobic property of a hydrophobic group, for example, ginsenoside, fat-soluble vitamins, antibiotics, enzymes, and phenolic compounds, may easily adsorb to the polystyrene resin. Next, distilled water having about a 5-fold volume of the resin capacity was allowed to flow through the column, and the aqueous component thus obtained was collected and freeze-dried to obtain 1.22 g of a HP-20 resin non-adsorption aqueous component. After removing the aqueous component, 20 to 50 v/v % ethanol having about a 5-fold to 10-fold volume of the resin was allowed to flow through the column including the resin adsorbed with HP-20 resin adsorption components, for example, hydrophobic saponin-based components, antioxidant components, and other hydrophobic components, to obtain an extract, and the extract was dried to obtain 0.93 g of a hydrophobic component fraction not including effective components. Then, 60 to 100 v/v % ethanol having about a 5-fold to 10-fold volume of the resin capacity was allowed to flow through the column to obtain an extract, and the extract was dried to obtain 0.61 g of a fraction including effective components. Amounts of Rg3, Rk1, and Rg5 with respect to a weight of Rb1, Rc, Rb2, Rd, Rg3, Rk1, and Rg5 in the prepared extract were 90% or more, as shown in Table 2.

COMPARATIVE EXAMPLE 1

Preparation of Cheong-Kwan-Jang's Red *Ginseng* Extract Pill Plus™ Freeze-dried Product A Cheong-Kwan-Jang's red *ginseng* extract pill Plus™ freeze-dried product was prepared to compare compositions of the microwave-irradiated products prepared according to Examples 1 and 2 with conventional heat-treated processed ginsengs, as follows. A *ginseng* extract of Cheong-Kwan-Jang's red *ginseng* extract pill Plus™ available in the market was freeze-dried to obtain a freeze-dried product of the Cheong-Kwan-Jang's red *ginseng* extract. Amounts of Rg3, Rk1, and Rg5 with respect to a weight of Rb1, Rc, Rb2, Rd, Rg3, Rk1, and Rg5 in the prepared extract were less than 90%.

EXAMPLE 3

Measurement of Cell Viability

1. Cell Culture
SK-MEL-2 human melanoma was available from the Korean Cell Line Bank (Seoul, Republic of Korea). The SK-MEL-2 human melanoma cells were incubated in RPMI-1640 (Roswell Park Memorial Institute medium, HyClone) containing 10% of fetal bovine serum (FBS) (HyClone), 200 IU/ml of penicillin, 200 mg/ml of streptomycin, 25 mM of sodium bicarbonate, and 25 mM of HEPES in a humidification culture vessel supplied with 5% $CO_2$/95% air at a temperature of 37° C. The culture medium was replaced with a new medium every two days.

2. Measurement of Cell Viability (MTT Analysis)
Measurement of human melanoma cell viability was performed by using a MTT staining method (J Immunol Methods, 141, 15-22, 1991). Human melanoma cells were dispensed into a 96-well plate at a density of 2×10$^4$ cells/well and then stabilized for 24 hours. A medium capacity of each well was equally 0.1 mL. As an experimental group, each of the *ginseng* extracts was dissolved in dimethylsulfoxide (DMSO) to be added at a concentration of 500, 400, 300, 250, 200, 150, 100, 50, or 25 ug/mL, and as a control group, only DMSO was used without adding a *ginseng* extract, and the samples were cultured for 24 hours. Here, the final content of DMSO was 0.5%. After 24 hours, 10 μl of MTT (5 mg MTT/1 mL in PBS) was added to the medium, and human melanoma cells were further incubated for 2 hours. The medium was removed from each well and was added to 100 μl of DMSO to perform mixing by pipetting to dissolve the reduced MTT solid. Each well was scanned by using a microplate reader having a 540 nm filter (Powerwave XS, Bio-tek) to measure fluorescence light emitted from the resultant, and thus relative human melanoma cell viabilities were calculated.

FIG. 1 is a view that shows the results of measured viabilities of human melanoma cells when cultured in the presence of various types of *ginseng* extracts. In FIG. 1, WG denotes white *ginseng*, and 300 g of dried *Panax ginseng* roots purchased from herbal medicine shops in the Geumsan *ginseng* market, Korea were added to 6.0 L of 50% ethanol, and the resultant mixture was reflux extracted at 80° C. for 3 hours to obtain a 50% ethanol extract. Thereafter, the obtained 50% ethanol extract was dried under reduced pressure to vaporize the solvent therefrom to obtain a dried extract, and a content of Rg3, Rk1, and Rg5 in the extract was less than 90% with respect to a weight of ginsenoside Rb1, Rb2, Rc, Rd, Rg1, and Re. RG denotes red *ginseng* which refers to a freeze-dried product of Cheong-Kwan-Jang's red *ginseng* prepared in Comparative Example 1. MG denotes microwaved *ginseng* which was prepared as described in Example 1. GF denotes a ginsenoside fraction that was microwaved as described in Example 2. In FIG. 1, a horizontal axis represents concentrations of a *ginseng* extract, and a vertical axis represents cell viabilities (%) with respect to the control group. As shown in FIG. 1, the microwave processed *Panax* spp. plant extract efficiently and concentration-dependently suppressed viability of skin cancer cells compared to those of the control group, white *ginseng*, or red *ginseng*, and this was unexpected but significant. $IC_{50}$ values of *ginseng* extracts with respect to human melanoma cells (SK-MEL-2) obtained from the results shown in FIG. 1 are shown in Table 3. Table 2 shows amounts (ug/ml) of ginsenoside of the *ginseng* extracts, respectively. WG, RG, MG, and GF in Tables 2 and 3 are the same as described in relation to FIG. 1.

TABLE 2

|     | Rb1   | Rc    | Rb2   | Rd    | Rg3    | Rk1    | Rg5    | (Rg5 + Rk1)/Rg3 | Amount* |
|-----|-------|-------|-------|-------|--------|--------|--------|-----------------|---------|
| WG  | 91.66 | 75.24 | 43.72 | 24.02 | N.D**  | N.D**  | N.D**  | 0               | 0       |
| RG  | 8.53  | 5.13  | 2.14  | 1.10  | 3.29   | 0.84   | 1.83   | 0.81            | 26.07   |
| MG  | 6.21  | 3.68  | 3.83  | 2.39  | 60.86  | 43.90  | 91.49  | 2.22            | 92.41   |
| GF  | N.D** | N.D** | N.D** | N.D** | 164.48 | 115.90 | 231.60 | 2.11            | 100     |

*Amount of Rg3, Rk1, and Rg5 with respect to a weight of Rb1, Rc, Rb2, Rd, Rg3, Rk1, and Rg5 (%)
**N.D: Not Detected

TABLE 3

| Ginseng extract | IC$_{50}$(ug/mL) |
|-----------------|------------------|
| WG              | 500>             |
| RG              | 500>             |
| MG              | 217.3            |
| GF              | 64.8             |

In Table 3, IC$_{50}$ denotes a half maximal inhibitory concentration.

As shown in Table 3, IC50 values of MG and GF have about ½ low concentrations, compared to those of WG and RG, and thus, have cell toxicity that is about twice or higher than that of human melanoma. This is an unexpectedly significant effect to those of ordinary skill in the art.

3. Measurement of Cell Shape

Human melanoma cells were dispensed into a 6-well plate at a density of 1×10$^5$ cells/well and stabilized for 24 hours. A capacity of medium in each well was equally 1 mL. As a control group, human melanoma cells grown in the same medium was used, except that a *ginseng* extract was not added. Various types of *ginseng* extracts were added to the 6-well at a concentration of 60 ug/mL, in the case of GF, or 200 ug/mL, in the cases of WG, RG, and MG, and the cells were cultured for 24 hours. Then, a shape of the human melanoma cells was observed by using an optical microscope (DM IL microscope, available from Leica, Wetzlar, German).

Figure 2:
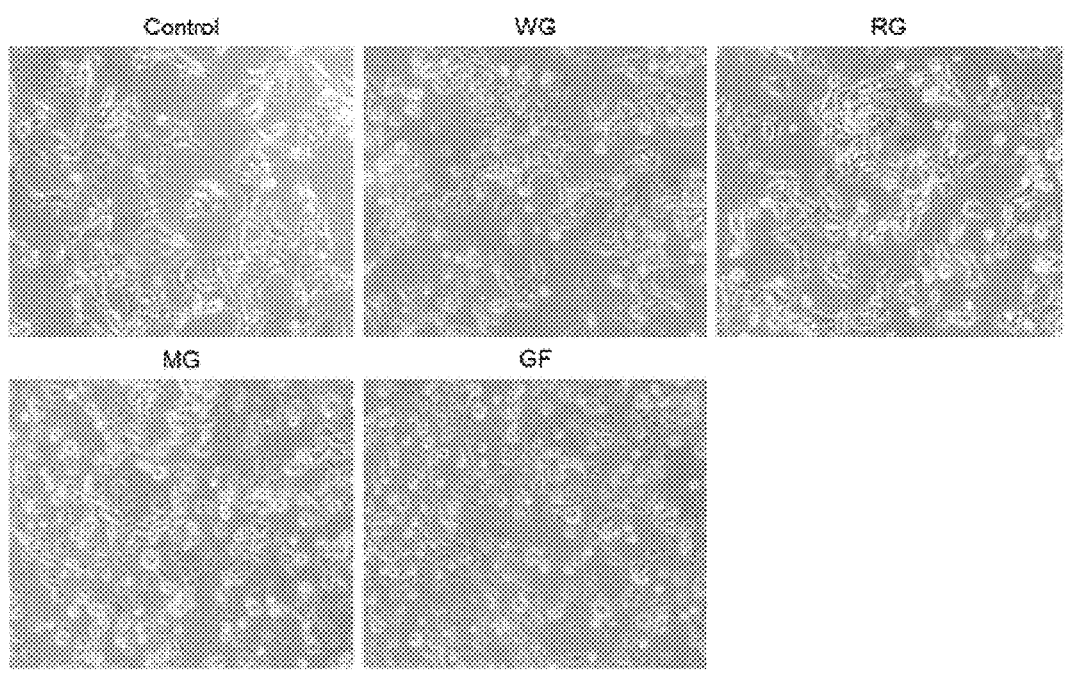
In FIG. 2, progression of apoptosis was observed by confirming a cell shape of human melanoma cells treated with the composition according to an embodiment of the present invention; and In FIG. 3, it was confirmed that the composition according to an embodiment of the present invention induces mitochondria-involved apoptosis by undergoing Bcl-2-associated X protein (Bax), which is a target protein of skin cancer cells, and poly ADP ribose polymerase (PARP) and thus activating caspase-3, by performing a western blot assay.

FIG. 2 is a view that illustrates the results of observing a shape of human melanoma cells when cultured in the presence of various types of *ginseng* extracts by using an optical microscope. In FIG. 2, WG, RG, MG, and GF are the same as described in relation to FIG. 1. As shown in FIG. 2, when MG and GF were used, the apoptotic bubble appearance significantly increased, compared to when MG and GF were not used.

EXAMPLE 4

Western Blotting

A western blotting analysis was performed on the human melanoma cells cultured according to Example 3. The cultured human melanoma cells were washed with a PBS solution and centrifuged at 3,000 rpm for 3 minutes. The cell pellet underwent lysis in a RIPA cell extract buffer at 4° C. for 20 minutes. The cell lysate was centrifuged at 4° C. for 10 minutes at 13,000 rpm, and a supernatant protein was separated in 10% sodium dodecyl sulfate polyacrylamide gel electrophoresis (SDS-PAGE) gel, and metastasized to a nitrocellulose membrane (Pall, Port Washington, N.Y., USA) at 200 mA for 2 hours. The membrane was blocked with 5% skim milk in Tween-20 containing Tris-buffered saline (TBST, 20 mM tris-HCl (pH 7.6)), and cultured with primary anti-human Bax, Bcl-2, PARP, caspase-3, and GAPDH antibody (Santa Cruz Biotechnology, California, USA) in TBST containing 5% skim milk. After being cultured with secondary horseradish peroxidase-conjugated anti-IgG antibody, an immune-detected protein was visualized by using an enhanced chemiluminescence kit (Amersham Life Science, Buckinghamshire, England).

Figure 3:
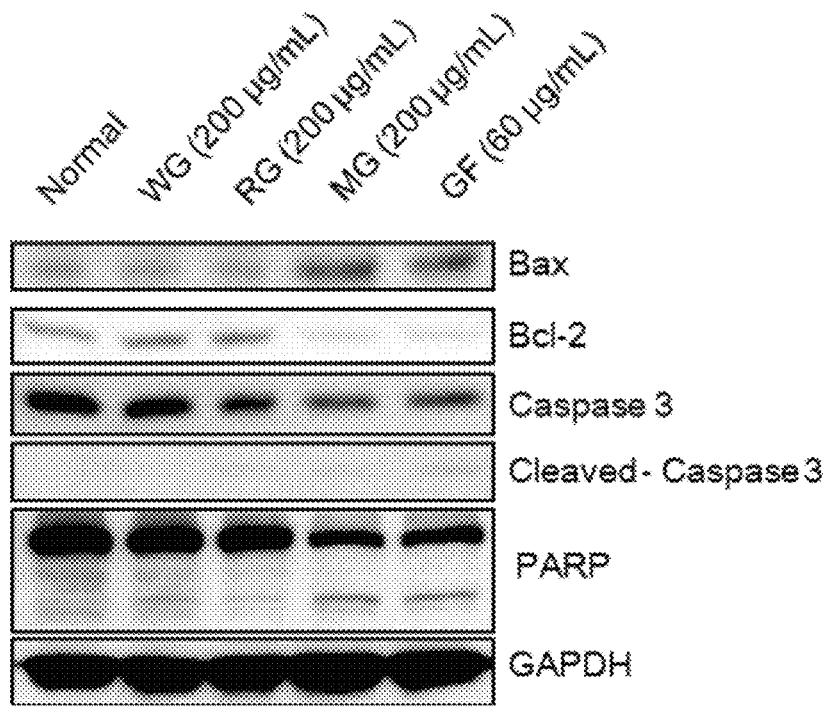

FIG. 3 is a view that illustrates the results of western blotting performed on human melanoma cells when cultured in the presence of various types of *ginseng* extracts. In FIG. 3 WG, RG, MG, and GF are the same as described in relation to FIG. 1, and Normal denotes a control group that is treated with DMSO only. A concentration shown in FIG. 3 denotes a concentration that is finally treated on the cells. As shown in FIG. 3, it may be confirmed that when MG and GF were used, Bax, caspase-3, and PARP involved in apoptosis were expressed. Thus, it was confirmed that mitochondria-involved apoptosis, which activates caspase-3, was induced through Bax and PARP by microwave-processed *Panax* spp. plant extract.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the inventive concept as defined by the following claims.

What is claimed is:

1. A method of preventing or treating skin cancer in a subject, the method comprising administering a therapeutically effective amount of a pharmaceutical composition to a subject having skin cancer, wherein the composition comprises a *Panax* spp. plant extract containing 100% of Rg3, Rk1, and Rg5 with respect to a weight of ginsenoside Rb1, Rc, Rb2, Rd, Rg3, Rk1, and Rg5, and wherein the ratio of Rg3, Rk1, and Rg5 content is 1.42: 1.00: 2.00, and the skin cancer is melanoma.

2. The method of claim 1, wherein the *Panax* spp. plant is *Panax ginseng, Panax quinquefolia, Panax notoginseng, Panax japonica, Panax trifolia, Panax pseudoginseng, Panax vietnamensis*, a cultured root thereof, a heat-treated or enzyme-treated process product thereof, or a combination thereof.

3. The method of claim 1, wherein the *Panax* spp. plant extract is a crude extract of water, C1-C4 alcohol, or a mixture thereof of any *Panax* spp. plant; a solvent fraction of n-hexane, methylenechloride, ethylacetate, butanol, or a mixture thereof of the crude extract; or a purified product of the solvent fraction.

* * * * *